United States Patent [19]

Morgan

[11] Patent Number: 4,724,239

[45] Date of Patent: Feb. 9, 1988

[54] METHOD OF TREATING CHEMICAL ULCERS WITH N,N'-DIACETYLCYSTINE, N-ACETYL HOMOCYSTEINE AND N-ACETYL CYSTEINE

[76] Inventor: Lee R. Morgan, 725 Topaz St., New Orleans, La. 70124

[21] Appl. No.: 776,579

[22] Filed: Sep. 16, 1985

[51] Int. Cl.$^4$ .......................................... A61K 31/195
[52] U.S. Cl. .................................................. 514/563
[58] Field of Search ........................................ 514/563

[56] References Cited

U.S. PATENT DOCUMENTS 4,331,648  5/1982  Myers, Jr. et al. ................... 424/10

OTHER PUBLICATIONS

Chemical Abstracts 96:15050x (1982).

Primary Examiner—Jerome D. Goldberg
Attorney, Agent, or Firm—Klarquist, Sparkman, Campbell, Leigh & Whinston

[57] ABSTRACT

A method of treating chemical ulcers caused by leukotriene production, the method comprising the step of applying to the ulcer a compound that interferes with leukotriene production, the compound being selected from the group consisting of N,N'-diacetylcystine, N-acetylhomocysteine and N-acetylcysteine.

15 Claims, No Drawings

METHOD OF TREATING CHEMICAL ULCERS WITH N,N'-DIACETYLCYSTINE, N-ACETYL HOMOCYSTEINE AND N-ACETYL CYSTEINE

BACKGROUND OF THE INVENTION

1. Field of the Invention

This invention relates to treatment of chemical ulcers, such as those caused by anthracyclines. More specifically, it concerns treatment of such ulcers with N,N'-Diacetylcystine, N-Acetyl Homocysteine and N-Acetyl Cysteine by interfering with leukotriene production.

2. General Background of the Invention

The anthracyclines have the general formula:

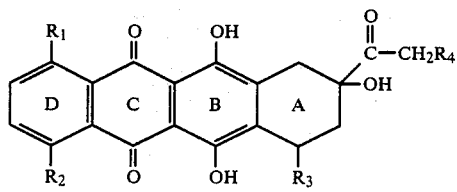

and their essential structure is based on the anthraquinone ring which characteristically has a quinone functionality on the C ring and a hydroquinone function on the B ring. In addition, a hexose sugar is commonly attached through a glycosidic linkage at $R_3$. Daunosamine is the most common sugar to be found at $R_3$, $R_1$, and $R_2$, while $R_4$ can vary widely. The two anthracyclines presently in clinical use are doxorubicin (marketed by Adria Laboratories of Dublin, Ohio as Adriamycin ™) and duanomycin. In doxorubicin, $R_1$, $R_2$, and $R_4$ are H, $OCH_3$, and OH; this structure is shown below:

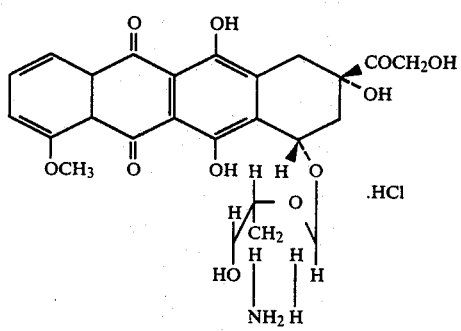

For duanomycin, $R_1$, $R_2$ and $R_4$ are H, $OCH_3$ and H, respectively, while $R_3$ is daunosamine.

The anthracyclines are members of the Rhodomycin group of antibiotics produced by Streptomyces. The anthracyclines are o interest because a number of them show considerable activity against a wide range of human and animal tumors. Two members of this group, daunomycin and doxorubicin (Adriamycin ™), are in widespread use in this country as anticancer agents. However, the clinical use of these drugs is impaired because they cause cardiac damage in both man and animals.

Another important toxicity associated with these agents is tissue necrosis, often requiring surgical debridement if the agents extravasate into subcutaneous tissue during intravenous injections. This problem is particularly harmful and painful since these chemical ulcers tend to last many months and usually require surgical debridement.

A number of agents have been injected or topically applied to animal models or clinical cases of Adriamycin ™ (ADM) skin necrosis. Sodium bicarbonate (Lancet, 2: 417, 1978), alpha tocopherol, beta adrengics, diphendydramine and cimetidine (Cancer Treat Rep. 65: 1001, 1981), DMSO (Cancer Treat Rep. 67: 407, 1983) and corticosteroids (Am. J. Nurs. 79: 94, 1979) have all been tried. For various reasons, none of these agents have been widely accepted.

N-acetylcysteine is an agent that has been extensively evaluated for all types of ADM toxicities. Unfortunately, previous reports have indicated that when NAC was injected intradermally just proximal to ADM induced ulcers in mice, the latter ulcers became worse (Cancer Treat. Rep. 65: 1001, 1981). With the exception of corticosteroids, surgical debridement and graft placement, there has been no satisfactory parenteral or topical formulation available for treating these chemical ulcers.

It is accordingly an object of this invention to provide a non-toxic, water soluble, tissue penetratable agent which is absorbed in effective amounts and that can promote tissue healing.

SUMMARY OF THE INVENTION

The aforementioned object has been achieved by topically applying N,N'-diacetylcystine (N-DAC), N-acetyl homocysteine (NAH) or N-acetylcysteine (NAC) to chemical ulcers caused by anthracyclines such as doxorubicin (Adriamycin ™) or duanomycin.

N,N'-diacetylcystine (N-DAC) has the following formula:

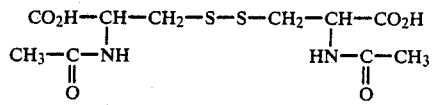

while N-acetyl homocysteine (NAH) having the formula:

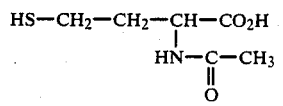

and N-acetyl cysteine (NAC) has the formula:

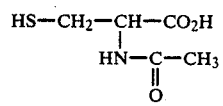

The present invention comprises using these compounds to block and reverse skin damage resulting from the use of anthracyclines, notably doxorubicin (Adriamycin ™). The compounds are applied to the ulcer to interfere with production of leukotrienes. In preferred embodiments the compound is applied to the chemical ulcer as a 20% aqueous solution four times a day. In especially preferred embodiments, it is applied with a gauze bandage that has been soaked in the compound.

DETAILED DESCRIPTION OF THE PREFERRED EMBODIMENT

The present invention became possible after the inventor determined that Adriamycin TM (hereinafter ADM) remains locally in the dermis after extravasation following venous injections, and that the presence of ADM is accompanied by elevated concentrations of tissue leukotrienes $A_4$ ($LTA_4$), $C_4$ ($LTC_4$) and $D_4$ ($LTD_4$). These results indicate that tissue damage is initiated by ADM induced leukotriene release and propagated by the continued presence of ADM. When N,N'-diacetyl cystine (N-DAC), N-acetylcysteine (NAC) or N-cetylhomocysteine (NAH) is applied topically to open ADM induced ulcers, inflammation is reduced and healing promoted without the need for surgical debridement and graft placement.

N-DAC, NAC and NAH are accordingly useful as agents to reverse anthracycline (ADM) induced skin necrosis while being well tolerated and absorbed in ulcers and open skin lesions. These actions apparently result from interaction between the agent and peroxides and leukotriene $A_4$ ($LTA_4$) to reduce toxic free radicals and interrupt the leukotriene cascade to the highly inflammatory slow releasing substances of anaphylaxis, (SRS)-$LTC_4$ and $LTD_4$. The aforementioned benefits are obtained without interfering with the anti-tumor activity of ADM. The drastic prior art treatments, such as surgical debridement, are thereby avoided.

It is important to note that detectable blood levels of NAC, NAH or N-DAC are not present following the application of 20% concentrations of these agents in water three times a day to patients with open ulcers. In a rabbit animal model that was described previously (Cancer Treat. Rep. 65: 1001, 1981) neither NAC, N-DAC or NAH could be detected in animals' circulation after topical application of 20% solution of the above agents to the surfaces of rabbit ears.

MECHANISM OF ACTION

The present inventor has demonstrated that as part of the inflammatory process, tissue membrane destruction releases arachidonic acid which results in leukotrienes. The leukotrienes are in turn mediators of ischemia, arterial constriction and epithelial destruction.

Leukotrienes (LTs) are members of the eicosanoid family, and are the major biologically active eicosanoids of the lipoxygenase pathway of arachidonic acid metabolism. This pathway is illustrated schematically below:

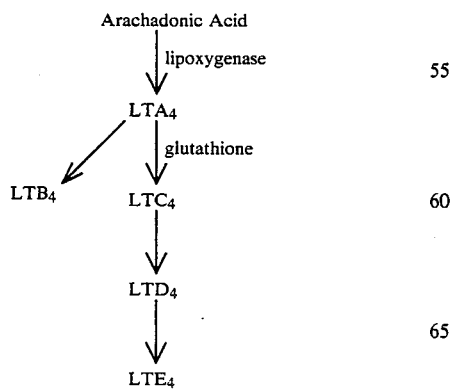

$LTA_4$ is the precursor of $LTB_4$, which is a potent chemotactic agent, and the LTs (i.e., $LTC_4$, $LTD_4$ and $LTE_4$), have been associated with the slow-reacting substances of anaphylaxis.

LTs are produced by a host of cell types, including the pulmonary parenchymal cells, macrophage, mast cells, leukocytes, connective tissue cells, and several types of smooth muscle cells, particularly vascular smooth muscle cells. When tissue and cellular membranes are destroyed by chemicals or other foreign irritations, arachidonic acid is released, thereby initiating the cascade to the leukotrienes and other chemical mediators of inflammation.

LTs exert a variety of biological actions that could contribute to their role as mediators of ischemia and shock. $LTB_4$ appears to play a key role as a mediator of inflammation by virtue of its chemotactic and chemokinetic properties on blood cells (e.g., eosinophils, macrophages). $LTB_4$ also promotes the release of lysosomal hydrolases from these and other cell types accompanied by an enhancement of microvascular permeability.

In contrast to $LTB_4$, the LTs (e.g. $LTC_4$, $LTD_4$, $LTE_4$) are more active as stimulators of smooth muscle contraction. $LTC_4$ is metabolized to $LTD_4$ and then to $LTE_4$, and there is a significant loss of biological activity as metabolism progresses. Although $LTC_4$ and $LTD_4$ are comparable to each other in activity, they are both much more active than $LTE_4$ in most biological systems.

$LTB_4$, $LTC_4$ and $LTD_4$ are mediators of inflammation. As long as these agents are produced because of continuous exposure to chemicals, the above LTs as well as other inflammatory factors will be produced. Of significant importance is that $LTC_4$ and $LTD_4$ are one in the same as the long acting substances of inflammation that also produce anaphylactic reactions to toxicity and drugs.

In the claimed embodiments, N-DAC, NAH or NAC can be used. Preferably N-DAC or NAH can be used, while most preferably N-DAC is used.

The present inventor has found that N-DAC and NAC interact with $LTA_4$ to produce a NAC adduct thus by-passing the formation of the tissue irritants $LTB_4$, $LTC_4$ and $LTD_4$. The identified $LTA_4$-NAC adduct is described below and has no inflammatory properties when injected into rabbit skin. The adduct which is obtained is shown below:

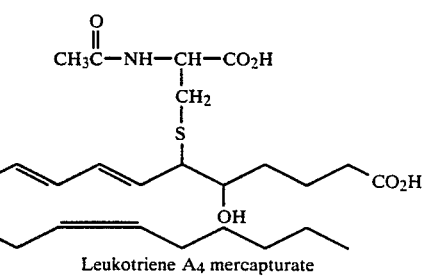

Leukotriene $A_4$ mercapturate

METHOD OF USE

Six patients were treated who were suffering from cutaneous ulcers produced following accidental extravasation of ADM during intravenous administration of the drug. To four of the patients, a 20% N-DAC (in water solution) was applied three times a day in the form of wet gauze compresses which remained in place.

Within 48–72 hours in all cases there was a reduction in pain, redness and inflammation. All lesions were cultured for bacterial contamination and where needed topical garamycin cream (0.1%) was applied twice daily along with the N-DAC solutions. All four patients demonstrated complete healing which did not require skin grafting. Debridement of scar formation was performed as needed to allow the deep penetration of N-DAC. A collagen scar was the result of the above applications of NAC.

Two additional patients with ADM-induced ulcers received topical applications of 20% NAC in water as continuous gauze soaks to the lesions. Both patients had permanent scar formation not requiring surgery following NAC application.

The importance of oral NAC on cardiac toxicities has been reported (U.S. Pat. No. 4,331,648) and shown not to reduce ADM antitumor activity. All six patients were continued on chemotherapy—three continued on Adriamycin TM combinations and three on 5-Fluorouracil, Cyclophosphamide and Methotrexate therapy. No changes in response patterns were seen in the patients.

Two of the six cases treated are described in more detail below.

Case Report 1

A 32 year old black female with advanced breast cancer developed a painful skin ulcer following inadvertent infiltration with ADM during her therapy. Accepted methods of treatment (intradermal sodium bicarbonate, dexamethasone, etc.) provided no relief, and she refused surgery. Gauze bandages soaked with N-DAC (20% solution) were applied four times a day over the ulcer. Over a 12 week period the lesion underwent scar formation and healed. The patient presently has complete leverage and rotation of the arm and wrist with complete scar formation.

Case Report 2

A 67 year old white female with advanced breast cancer which had spread to the lung was treated with ADM. During her therapy, a significant amount of ADM extravasated into her forearm. Over a one month period a large ulcer formed, but she was not a candidate for general surgery to repair the lesion. She was treated with 20% NAC in water topically. The solution was applied three times a day to gauze pads over the lesion for two months. There was immediate reduction in pain and redness followed by continuous scar formation with epithelialization and granulation until a permanent scar resulted that allowed free motion.

STARTING MATERIALS

NAC is commercially available from Aldrich Chemical Company, Milwaukee, Wis. It is the acetyl amide of the amino acid cysteine. Its use has predominantly been as a mucolytic agent in the treatment of bronchial compestion and bronchitis.

NAH can be purchased from Fluka Chemical Company of Switzerland.

N-DAC can be synthesized in the following manner. l-Cystine (0.05 mole, 12 g) was suspended in 50 ml of water and dissolved by adding 8M potassium hydroxide until the solution was pH 12. At 0° C. to 3° C., acetic anhydride (0.15 mole 15.3 g) was added in small portions as the pH of the solution was maintained between 10 and 10.5 with 8M potassium hydroxide. After the addition of acetic anhydride, the solution was allowed to stand one hour at room temperature at pH 10 and then adjusted to pH 3 with concentrated hydrochloric acid. The solution was concentrated in vacuo, and the viscous residue extracted three times with 100 ml portions of an acetone-water mixture (93:7 v/v). The acetone extract was concentrated in vacuo and dried in a desiccator over phosphorus pentoxide and sodium hydroxide. The residue was dissolved in ethanol. The precipitate that formed was removed by centrifugation and the remaining solution chromatographed on Silica Gel-G (Woelin). The columns were developed with chloroform:methanol:acetic acid (80:15:10 v/v). The columns were cut at $R_f=0.4$ and the N-DAC eluted with methanol. The methanol eluent was concentrated in vacuo to dryness over phosphorus pentoxide. The residue was dissolved in ethanol and the disulfide precipitated by adding the ethanolic solution to diethyl ether.

Yield 22%, m.p. 273–275, anal. calc. for $C_{10} H_{16} N_2 S_2 O_6$: C, 35.46; H, 5–20; N, 8–27%.

Found: C, 35–94; H, 5.24; N, 8.17%.

I claim:

1. A method of treating chemical ulcers in warm-blooded animals caused by leukotriene production, the method comprising the step of:
    topically applying to the ulcer an amount of a compound sufficient to interfere with leukotriene production and promote healing of the ulcer, the compound being selected from the group consisting of N,N'-diacetylcystine, N-acetyl homocysteine and N-acetyl cysteine.
2. The method of claim 1 wherein the compound is applied in the form of a 20% aqueous solution.
3. The method of claim 2 wherein the compound is applied four times a day.
4. The method of claim 3 wherein the compound is applied with gauze bandages soaked with the compound.
5. The method of claim 1 wherein the compound is N-acetylhomocysteine.
6. The method of claim 1 wherein the compound is N,N'-diacetylcystine.
7. A method of treating chemical ulcers in warm-blooded animals which have been caused by anthracycline, the method comprising the step of:
    topically applying to chemical ulcers which have been caused by an anthracycline an amount of a compound sufficient to promote healing of the ulcer, the compound being selected from the group consisting of N,N'-diacetylcystine, N-acetyl homocysteine and N-acetyl cysteine.
8. The method of claim 7 wherein the compound is applied in the form of a 20% aqueous solution.
9. The method of claim 8 wherein the compound is applied four times a day.
10. The method of claim 9 wherein the compound is applied with gauze bandages soaked with the compound.
11. The method of claim 7 wherein the compound is N-acetylhomocysteine.
12. The method of claim 7 wherein the compound is N,N'-diacetylcystine.
13. A method of treating chemical ulcers in warm-blooded animals which have been caused by anthracycline and which produce leukotrienes including $LTA_4$, comprising the step of:
    forming an adduct between $LTA_4$ and an amount of a compound selected from the group consisting of N,N'-diacetylcystine, N-acetyl homocysteine and N-acetyl cysteine sufficient to promote healing of the ulcer.

14. The method of claim 13 wherein the compound is N-acetylhomocysteine.

15. The method of claim 13 wherein the compound is N,N'-diacetylcystine.

* * * * *